(12) United States Patent
Derryberry et al.

(10) Patent No.: US 9,290,465 B2
(45) Date of Patent: Mar. 22, 2016

(54) SUBSTITUTED ISOXAZOLE AMINE COMPOUNDS AS INHIBITORS OF SCD1

(71) Applicant: Hoffmann-La Roche Inc., Nutley, NJ (US)

(72) Inventors: JohnMark Derryberry, Chicago, IL (US); Shawn David Erickson, Leonia, NJ (US); Paul Gillespie, Westfield, NJ (US); Eric Mertz, Fair Lawn, NJ (US)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 0 days.

(21) Appl. No.: 14/443,849

(22) PCT Filed: Nov. 29, 2013

(86) PCT No.: PCT/EP2013/075035
§ 371 (c)(1),
(2) Date: May 19, 2015

(87) PCT Pub. No.: WO2014/086667
PCT Pub. Date: Jun. 12, 2014

(65) Prior Publication Data
US 2015/0315160 A1 Nov. 5, 2015

Related U.S. Application Data

(60) Provisional application No. 61/732,463, filed on Dec. 3, 2012.

(51) Int. Cl.
*C07D 261/14* (2006.01)
*C07D 413/04* (2006.01)
*C07D 413/12* (2006.01)

(52) U.S. Cl.
CPC ............ *C07D 261/14* (2013.01); *C07D 413/04* (2013.01); *C07D 413/12* (2013.01)

(58) Field of Classification Search
None
See application file for complete search history.

(56) References Cited

PUBLICATIONS

Aliabiev et al., 4(3) Letts. Org. Chem. 203-211 (2007) (CAS Abstract).*

* cited by examiner

*Primary Examiner* — Timothy R Rozof

(57) ABSTRACT

The invention is concerned with a compound of formula (I) wherein R1 to R3 are defined as in the description and in the claims. The compound of formula (I) can be used as a medicament.

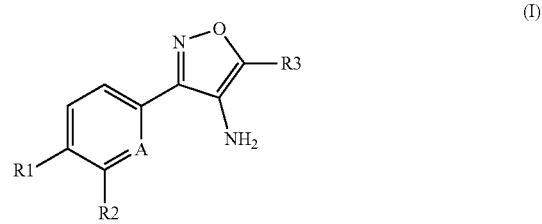

14 Claims, No Drawings

SUBSTITUTED ISOXAZOLE AMINE COMPOUNDS AS INHIBITORS OF SCD1

This application is a National Stage Application of PCT/EP2013/075035 filed Nov. 29, 2013, which claims priority from U.S. Provisional Patent Application No. 61/732,463, filed on Dec. 3, 2012. The priority of both said PCT and U.S. Provisional Patent Application are claimed. Each of the prior mentioned applications is hereby incorporated by reference herein in its entirety.

The present invention relates to organic compounds useful as inhibitors of Stearoyl-CoA desaturase 1 (SCD1) for the treatment of diseases such as, for example, cancer. In particular, the invention relates to substituted isoxazole amine compounds, their manufacture, pharmaceutical compositions containing them and methods of use.

The invention relates in particular to a compound of formula (I)

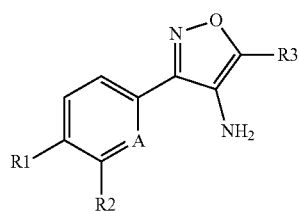

wherein
A is —CH— or nitrogen;
R1 is —O(CH$_2$)$_n$R4, —CH$_2$NHR4, —CH$_2$CH$_2$R4, —OCH$_2$C(O)R4 or —CH$_2$OR4;
R2 is hydrogen or halogen;
R3 is hydrogen or lower alkyl;
R4 is phenyl, pyridinyl, 1,1-dioxo-2,3-dihydro-1H-1lambda*6*-benzo[b]thiophenyl or 1,1-dioxo-1H-1lambda*6*-benzo[b]thiophenyl, said phenyl optionally mono- or bi-substituted independently with halogen, lower alkyl, alkoxy, —C(O)OCH$_3$, —S(O)$_2$CH$_3$, —NO$_2$, —CN, —CF$_3$, —OCF$_3$, —SCH$_3$, —SO$_2$-phenyl, —SCF$_3$ or —SO$_2$CH$_2$CH$_3$; and
n is 1, 2 or 3;
or a pharmaceutically acceptable salt thereof.

Cancer is a broad range of diseases, all of which are defined by unregulated growth and spread of abnormal cells. In cancer, cells divide and grow uncontrollably, forming malignant tumors, and invade nearby parts of the body. In the United States alone in 2012, approximately 600,000 deaths will result from cancer. [American Cancer Society. *Cancer Facts & Figures* 2012. Atlanta: American Cancer Society; 2012.]

The fate of the cell is the function of highly regulated activation and deactivation of both biosynthetic and energy-generating metabolic pathways. In mammals, cell growth, proliferation and survival require the formation of new cell membranes, which, in turn, entails the production of the appropriate lipids for a fully functional cell membrane. Saturated fatty acids (SFAs) and monounsaturated fatty acids (MUFAs) are the major fatty acid species in mammalian cellular lipids. As building blocks of phospholipids, diacylglycerols, triacylglycerols and cholesteryl esters, SFAs and MUFAs are fundamental building blocks of membrane structures and are critical mediators/regulators of myriad cellular activities. Because changes in the balance of SFA and MUFA in lipids can influence this wide array of cellular functions, the composition and distribution of SFA and MUFA within cells must be tightly regulated. Cellular lipids, including mono-unsaturated fatty acids and saturated fatty acids, have been linked to tumor cell proliferation and tumor cell survival due to their dual roles as 1) sources of metabolic energy and 2) mediators of cell signaling pathways. One key regulator of the fatty acid composition of cellular lipids is stearoyl-CoA desaturase 1 (SCD1) which catalyzes the introduction of the first double bond in the cis-delta-9 position of several saturated fatty acyl-CoAs, principally palmitoyl-CoA and stearoyl-CoA, to yield palmitoleoyl- and oleoyl-CoA, respectively. [R. A. Igal *Carcinogenesis* 2010, 31, 1509-1515].

The human SCD1 gene is ubiquitously expressed, with highest levels in brain, liver, heart and lung. SCD1 is highly expressed in oncogene-transformed lung fibroblasts and in cancer cells. SCD1 has been identified as an enzyme in the fatty acid synthesis pathway that is essential for cancer cell viability [Mason P, Liang B, Li L, Fremgen T, Murphy E, et al. PLoS ONE 2012, 7(3): e33823]. As an important regulator of the composition of cellular lipids, SCD1 has been proposed as a target for cancer therapies.

It has been demonstrated that SCD1 mRNA levels are elevated in tumors and that inhibition of SCD1 with siRNA or a small molecule inhibitor results in strong induction of apoptosis and growth inhibition. [U. V. Roongta et al. *Molecular Cancer Research* 2011, 9, 1551-1561]. It would be useful, therefore, to provide small molecule inhibitors of SCD1 for the treatment of cancer.

The invention also provides for pharmaceutical compositions comprising the compounds, methods of using the compounds and methods of preparing the compounds.

Unless otherwise indicated, the following specific terms and phrases used in the description and claims are defined as follows.

The term "moiety" refers to an atom or group of chemically bonded atoms that is attached to another atom or molecule by one or more chemical bonds thereby forming part of a molecule. For example, the R variables of formula I refer to moieties that are attached to the core structure of formula I by a covalent bond.

In reference to a particular moiety with one or more hydrogen atoms, the term "substituted" refers to the fact that at least one of the hydrogen atoms of that moiety is replaced by another substituent or moiety. For example, the term "lower alkyl substituted by halogen" means that one or more hydrogen atoms of a lower alkyl (as defined below) is replaced by one or more halogen atoms (e.g., trifluoromethyl, difluoromethyl, fluoromethyl, chloromethyl, etc.).

The term "alkyl" refers to an aliphatic straight-chain or branched-chain saturated hydrocarbon moiety having 1 to 20 carbon atoms. In particular embodiments the alkyl has 1 to 10 carbon atoms.

The term "lower alkyl" refers to an alkyl moiety having 1 to 7 carbon atoms. In particular embodiments the lower alkyl has 1 to 4 carbon atoms and in other particular embodiments the lower alkyl has 1 to 3 carbon atoms. Examples of lower alkyls include methyl, ethyl, propyl, isopropyl, butyl, isobutyl, sec-butyl and tert-butyl. Particular examples of "lower alkyl" are methyl, ethyl and isopropyl.

The term "alkoxy" denotes a group of the formula —O—R', wherein R' is an alkyl group. Examples of alkoxy moieties include methoxy, ethoxy, isopropoxy, and tert-butoxy. A particular example of "alkoxy" is methoxy.

"Aryl" means a monovalent cyclic aromatic hydrocarbon moiety having a mono-, bi- or tricyclic aromatic ring. The aryl group can be optionally substituted as defined herein. Examples of aryl moieties include, but are not limited to, phenyl, naphthyl, phenanthryl, fluorenyl, indenyl, pentalenyl, azulenyl, oxydiphenyl, biphenyl, methylenediphenyl, aminodiphenyl, diphenylsulfanyl, diphenylsulfonyl, diphenylisopropylidenyl, benzodioxanyl, benzofuranyl, benzodioxylyl, benzopyranyl, benzoxazinyl, benzoxazinonyl, benzopiperidinyl, benzopiperazinyl, benzopyrrolidinyl, benzomorpholinyl, methylenedioxyphenyl, ethylenedioxyphenyl, and the like, including partially hydrogenated derivatives thereof, each being optionally substituted.

The terms "halo", "halogen" and "halide", which may be used interchangeably, refer to a substituent fluoro, chloro, bromo or iodo. Particular "halogen" are fluoro, chloro and iodo.

The term sulfonyl, alone or in combination, means the —$SO_2$— group.

The term sulfonyl, alone or in combination, means the —S— group.

Unless otherwise indicated, the term "hydrogen" or "hydro" refers to the moiety of a hydrogen atom (—H) and not $H_2$.

Unless otherwise indicated, the term "a compound of the formula" or "a compound of formula" or "compounds of the formula" or "compounds of formula" refers to any compound selected from the genus of compounds as defined by the formula (including any pharmaceutically acceptable salt or ester of any such compound if not otherwise noted).

The term "pharmaceutically acceptable salts" refers to those salts which retain the biological effectiveness and properties of the free bases or free acids, which are not biologically or otherwise undesirable. Salts may be formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, N-acetylcystein and the like. In addition, salts may be prepared by the addition of an inorganic base or an organic base to the free acid. Salts derived from an inorganic base include, but are not limited to, the sodium, potassium, lithium, ammonium, calcium, and magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like. Particular examples of pharmaceutically acceptable salts of the compound of formula (I) are the hydrochloride and the trifluoroacetic acid salts.

The compounds of the present invention can be present in the form of pharmaceutically acceptable salts. The compounds of the present invention can also be present in the form of pharmaceutically acceptable esters (i.e., the methyl and ethyl esters of the acids of formula I to be used as prodrugs). The compounds of the present invention can also be solvated, i.e. hydrated. The solvation can be effected in the course of the manufacturing process or can take place i.e. as a consequence of hygroscopic properties of an initially anhydrous compound of formula I (hydration).

Compounds that have the same molecular formula but differ in the nature or sequence of bonding of their atoms or the arrangement of their atoms in space are termed "isomers" and fall within the scope of the invention. Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, 1 mg to about 1,000 mg, or 1 mg to 100 mg may be appropriate, although the lower and upper limits may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention is contemplated. Supplementary active compounds can also be incorporated into the compositions.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

In the practice of the method of the present invention, an effective amount of any one of the compounds of this invention or a combination of any of the compounds of this invention or a pharmaceutically acceptable salt or ester thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form of solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

The invention relates in particular to:

A compound of formula (I) wherein A is —CH—;

A compound of formula (I) wherein R1 is —O(CH$_2$)$_n$R4 or —CH$_2$NHR4;

A compound of formula (I) wherein R1 is —O(CH$_2$)$_n$R4;

A compound of formula (I) wherein R1 is —OCH$_2$R4;

A compound of formula (I) wherein R2 is hydrogen;

A compound of formula (I) wherein R3 is lower alkyl;

A compound of formula (I) wherein R3 is hydrogen or methyl;

A compound of formula (I) wherein R3 is methyl;

A compound of formula (I) wherein R4 is unsubstituted phenyl, pyridinyl, 1,1-dioxo-2,3-dihydro-1H-1lambda*6*-benzo[b]thiophenyl or 1,1-dioxo-1H-1lambda*6*-benzo[b]thiophenyl;

A compound of formula (I) wherein R4 is unsubstituted phenyl;

A compound of formula (I) wherein R4 is phenyl mono-substituted with Cl, F, I, methyl, isopropyl, —OCH$_3$, —C(O)OCH$_3$, —S(O)$_2$CH$_3$, —NO$_2$, —CN, —CF$_3$, —OCF$_3$, —SCH$_3$, —SO$_2$-phenyl, —SCF$_3$ or —SO$_2$CH$_2$CH$_3$;

A compound of formula (I) wherein R4 is phenyl bi-substituted independently with methyl or halogen; and A compound of formula (I) wherein R4 is fluorophenyl, phenyl, methoxyphenyl, methoxycarbonylphenyl, methylsulfonylphenyl, pyridinyl, nitrophenyl, cyanophenyl, trifluoromethylphenyl, trifluoromethoxyphenyl, difluorophenyl, chloropenyl, dimethylphenyl, dichlorophenyl, methylphenyl, iodophenyl, isopropylphenyl, ethylsulfonylphenyl, 1,1-dioxo-2,3-dihydro-1H-1lambda*6*-benzo[b]thiophenyl, 1,1-dioxo-1H-1lambda*6*-benzo[b]thiophenyl, phenylsulfonylphenyl, methylsulfonylphenyl or trifluoromethylsulfonylphenyl.

The invention further relates to a compound of formula (I) selected from
3-[4-(4-Fluoro-benzyloxy)-phenyl]-isoxazol-4-ylamine;
3-(4-Benzyloxy-phenyl)-isoxazol-4-ylamine;
3-[4-(4-Methoxy-benzyloxy)-phenyl]-isoxazol-4-ylamine;
4-[4-(4-Amino-isoxazol-3-yl)-phenoxymethyl]-benzoic acid methyl ester hydrochloride;
3-[4-(4-Methanesulfonyl-benzyloxy)-phenyl]-isoxazol-4-ylamine;
3-{4-[(4-methanesulfonyl-phenylamino)-methyl]-phenyl}-isoxazol-4-ylamine hydrochloride;
3-[4-(2-Chloro-4-methanesulfonyl-benzyloxy)-phenyl]-isoxazol-4-ylamine;
3-{4-[2-(4-Methanesulfonyl-phenyl)-ethyl]-phenyl}-isoxazol-4-ylamine;
3-(5-Phenethyloxy-pyridin-2-yl)-isoxazol-4-ylamine;
3-[4-(3-Phenyl-propoxy)-phenyl]-isoxazol-4-ylamine;
3-[5-(4-Methanesulfonyl-benzyloxy)-pyridin-2-yl]-isoxazol-4-ylamine;
3-[4-(4-Methanesulfonyl-benzyloxy)-phenyl]-5-methyl-isoxazol-4-ylamine;
3-[4-(Pyridin-3-ylmethoxy)-phenyl]-isoxazol-4-ylamine;
2-[4-(4-Amino-isoxazol-3-yl)-phenoxy]-1-phenyl-ethanone hydrochloride;
3-[4-(4-Nitro-benzyloxy)-phenyl]-isoxazol-4-ylamine hydrochloride;
4-[4-(4-Amino-isoxazol-3-yl)-phenoxymethyl]-benzonitrile hydrochloride;
3-[4-(4-Amino-isoxazol-3-yl)-phenoxymethyl]-benzonitrile hydrochloride;
3-[4-(4-Trifluoromethyl-benzyloxy)-phenyl]-isoxazol-4-ylamine hydrochloride;
3-[4-(4-Trifluoromethoxy-benzyloxy)-phenyl]-isoxazol-4-ylamine hydrochloride;
3-[4-(3,5-Difluoro-benzyloxy)-phenyl]-isoxazol-4-ylamine hydrochloride;
3-[4-(2-Chloro-benzyloxy)-phenyl]-isoxazol-4-ylamine hydrochloride;
3-[4-(3,4-Dimethyl-benzyloxy)-phenyl]-isoxazol-4-ylamine hydrochloride;
3-[4-(3-Trifluoromethoxy-benzyloxy)-phenyl]-isoxazol-4-ylamine hydrochloride;
3-[4-(4-Chloro-benzyloxy)-phenyl]-isoxazol-4-ylamine;
3-[4-(3,4-Dichloro-benzyloxy)-phenyl]-isoxazol-4-ylamine hydrochloride;
3-[4-(4-Methyl-benzyloxy)-phenyl]-isoxazol-4-ylamine hydrochloride;
3-[4-(4-Iodo-benzyloxy)-phenyl]-isoxazol-4-ylamine;
3-[4-(4-Isopropyl-benzyloxy)-phenyl]-isoxazol-4-ylamine;
3-[4-(4-Methanesulfonyl-benzyloxy)-phenyl]-isoxazol-4-ylamine hydrochloride;
3-[4-(4-Ethanesulfonyl-benzyloxy)-phenyl]-isoxazol-4-ylamine;
3-[4-(1,1-Dioxo-2,3-dihydro-1H-1lambda*6*-benzo[b]thiophen-5-ylmethoxy)-phenyl]-isoxazol-4-ylamine;
3-[4-(1,1-Dioxo-1H-1lambda*6*-benzo[b]thiophen-5-ylmethoxy)-phenyl]-isoxazol-4-ylamine;
3-[4-(4-Benzenesulfonyl-benzyloxy)-phenyl]-isoxazol-4-ylamine;
3-[4-(4-Methylsulfanyl-benzyloxy)-phenyl]-isoxazol-4-ylamine; and
3-[4-(4-Trifluoromethylsulfanyl-benzyloxy)-phenyl]-isoxazol-4-ylamine.

The invention further relates to:

A pharmaceutical composition, comprising a therapeutically effective amount of a compound of formula (I) and a pharmaceutically acceptable carrier;

A compound of formula (I) for use as a therapeutically active substance;

A compound of formula (I) for use as a therapeutically active substance in the treatment of cancer;

The use of a compound of formula (I) for the treatment of cancer;

The use of a compound of formula (I) for the preparation of a medicament for the treatment cancer; and A method for treating cancer, comprising the step of administering a therapeutically effective amount of a compound of formula (I) to a subject in need thereof.

The compound of the invention can be prepared using methods known to the skilled person. The compound of formula (I) can be prepared in particular according to the following method.

The starting materials and reagents used in preparing the compounds of the invention generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40.

The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Compounds of the present invention can be prepared beginning with commercially available starting materials and utilizing general synthetic techniques and procedures known to those skilled in the art. Outlined below are reaction schemes suitable for preparing such compounds. Further exemplification is found in the specific examples listed below.

Scheme 1

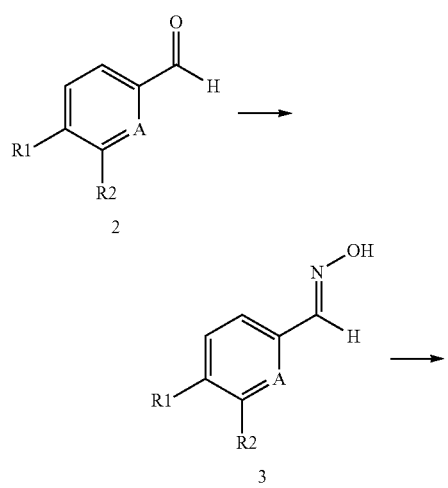

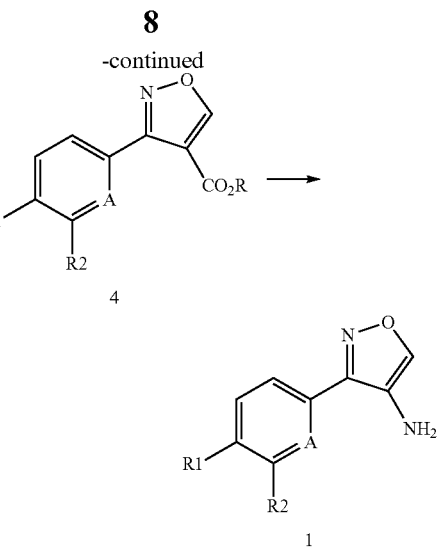

Compounds of the invention may be made by any conventional means. For example, they may be made according to the process outlined in Scheme 1, where A, R1, and R2 are as described above. According to this process, an aldehyde of formula 2, is treated with hydroxylamine to form the oxime of formula 3, which undergoes oxidation with an oxidant such as N-chlorosuccinimide followed by a [2,3]-dipolar cycloaddition with an acetylene equivalent containing an appropriate regiochemical directing group such as 3-dimethylamino-acrylic acid ethyl ester or 3-methoxyacrylic acid methyl ester to give the compound of formula 4. The ester can be converted to the amino group by well-established methods such as hydrolysis and rearrangement to give compounds of the invention of formula 1. The formation of the oxime of formula 3 can be conveniently effected by treating the aldehyde of formula 2 with hydroxylamine hydrochloride in the presence of an inorganic base such as sodium acetate or sodium hydroxide in an inert solvent such as an alcohol (e.g., methanol or ethanol or tert-butanol) or a mixture of such an alcohol and water at a temperature or in the presence of an organic base such as triethylamine or diisopropylethylamine in a solvent such as dichloromethane or in pyridine between about rt and about the reflux temperature of the solvent(s). Examples of conditions for such a reaction can be found in the literature, for example in Kao, Y. T. R. et al. US 20110212975; in Charrier, J.-D. et al. WO2011/143426; in Nakano, Y. et al. *J. Med. Chem.* 2006, 49, 2398-2406 and in Liu, K. C. et al. *J. Org. Chem.* 1980, 45, 3916-3918. A wide variety of aldehydes of formula 2 are commercially available including but not limited to the following: 4-hydroxybenzaldehyde, 4-cyanobenzaldehyde, 4-((4-methoxybenzyl)oxy)benzaldehyde, 5-hydroxypyridine-2-carbaldehyde and 4-methoxybenzaldehyde.

The reaction of an oxime of formula 3 to give an isoxazole of formula 1 can be carried out using a [2,3]-dipolar cycloaddition reaction. The oxime of formula 3 is first treated with an oxidizing agent such as sodium hypochlorite or N-chlorosuccinimide in an inert solvent such as DMF at about rt to form the oximinoyl chloride. This is then treated with 3-dimethylamino-acrylic acid ethyl ester. It will be apparent to one of average skill in the art of organic synthesis that the oximinoyl chloride can also undergo a [2,3]-dipolar cycloaddition with a lower alkyl ester of 3-dialkylamino- or alkoxyacrylic acid alkyl ester such as such as the N,N-dimethyl or diethyl amino or methyl or ethyl esters or 3-ethoxyacrylic acid ethyl ester to give the compound of formula 4, as shown in Scheme 2. It is commonly run in the presence of an organic base such as triethylamine. This particular cycloaddition is well-known to those skilled in the art of organic synthesis and can be run in a variety of solvents, for example, dichloromethane or toluene and at ambient temperatures such as 40° C. Examples of these conditions can be found in Bystroem, S. et al, PCT Int. Appl., 2009090239, 23 Jul. 2009 and Yamamoto, Takashi et al. Bioorganic & Medicinal Chemistry Letters, 17(13), 3736-3740; 2007. The reaction may also be run using an alkyl propiolate as a reaction partner but it has long been established in the chemical literature that these conditions often do not cleanly give the desired regiochemistry. For R3-substituted isoxazoles, an appropriately substituted olefin-containing reactant, such as crotonates for R3=—CH3, could be used to provide a variety of R3 groups.

Scheme 2

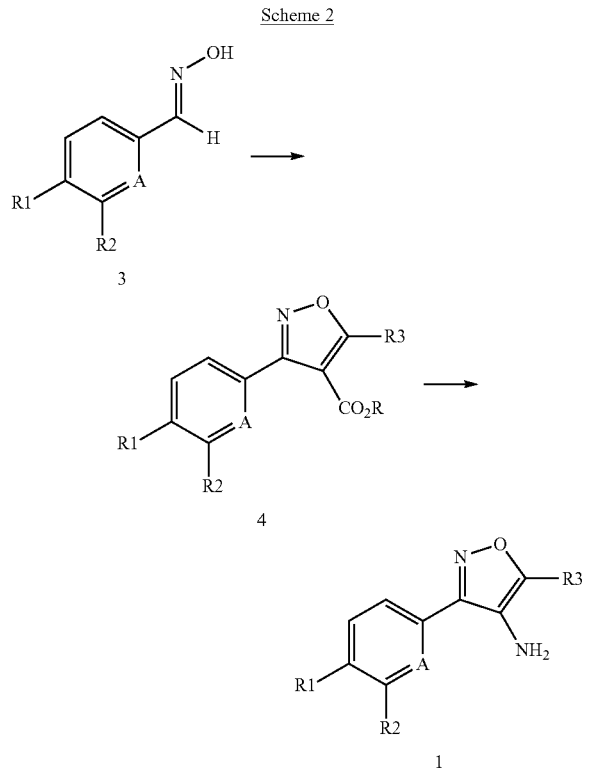

Transformation from intermediates of formula 4 to products of formula 1 may be effected by a variety of well-established methods familiar to practitioners of synthetic organic chemistry. The Hofmann, Curtis and Schmidt rearrangements are conversions from carboxylic acid equivalents to amines and have been part of the synthetic repertoire since they were reported in the chemical literature in and 1881, 1890 and 1924 respectively. It has been subsequently shown that carrying out such reactions in the presence of an alcohol, such as tert-butanol, provides the corresponding carbamate as the product. Carbamates such as tert-butyl carbamates and benzyl carbamates have found wide utility as protecting groups in the synthetic organic chemistry.

Scheme 3

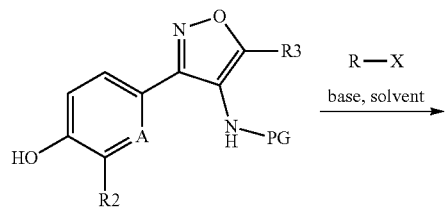

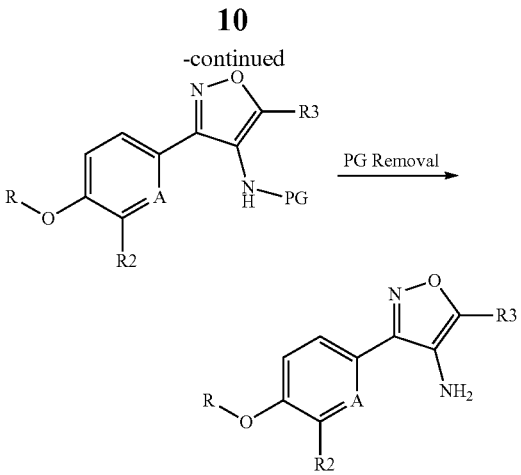

Phenol alkylation as shown in Scheme 3 could be carried out using a number of known methods, for example, stirring the phenol and an electrophile such as a substituted benzyl bromide, tosylate or chloride in a polar solvent such as DMF or isopropyl alcohol in the presence of an inorganic base such as potassium carbonate or sodium phosphate or, alternatively, an organic base such as triethylamine. A catalyst such as tetrabutylammonium iodide may be used. A nitrogen protecting group (designated PG in Scheme 3) such as a tert-butyl or benzylcarbamate may be present and removed by methods familiar to those skilled in the art of organic synthesis in the step following the alkylation. A wide variety of benzyl halides and alkyl halides used in preparing the SCD1 inhibitors described are commercially available including but not limited to 4-(methylsulfonyl)benzylbromide, 4-(ethylsulfonyl)benzylbromide, 1-bromomethyl-2-chloro-4-methanesulfonyl-benzene, 3-phenyl-1-bromopropane, 4-bromomethylbenzenesulfonamide, 3-cyanobenzyl bromide, 4-(trifuloromethylthio)benzyl bromide and 2-bromoacetophenone.

The invention will now be illustrated by the following examples which have no limiting character.

EXAMPLES

Although certain exemplary embodiments are depicted and described herein, the compounds of the present invention can be prepared using appropriate starting materials according to the methods described generally herein and/or by methods available to one of ordinary skill in the art.

The following abbreviations are used in the experimental section

| | |
|---|---|
| AcOH | acetic acid |
| BBr3 | boron tribromide |
| Calcd. | calculated |
| CH2Cl2 | dichloromethane |
| CH3CN | acetonitrile |
| CH3OH | methanol |
| CHCl3 | chloroform |
| DMF | dimethylformamide |
| DMSO | dimethylsulfoxide |
| ESI | electrospray ionization |
| Et2O | diethyl ether |
| EtOAc | ethyl acetate |
| g | grams |
| h | hours |
| H2O | water |
| HCl | hydrochloric acid |
| HF | hydrogen fluoride |

| | |
|---|---|
| HRMS | High-resolution mass spectrum |
| KF | potassium fluoride |
| KHCO$_3$ | potassium hydrogen carbonate |
| KOH | potassium hydroxide |
| LRMS | low-resolution mass spectrum |
| M | molar |
| m/z | mass divided by charge |
| M$^+$ | positively charged molecular ion |
| MCPBA | meta-chloroperoxybenzoic acid |
| MeOH | methanol |
| mg | milligrams |
| min | minutes |
| mL | milliliters |
| mmol | millimoles |
| MnO$_2$ | manganese dioxide |
| mp | melting point |
| Na$_2$CO$_3$ | sodium carbonate |
| Na$_2$SO$_3$ | sodium thiosulfate |
| Na$_2$SO$_4$ | sodium sulfate |
| NaH | sodium hydride |
| NaHCO$_3$ | sodium hydrogen carbonate |
| Na(OAc)$_3$BH | sodium triacetoxyborohydride |
| NaOH | sodium hydroxide |
| NH$_3$ | ammonia |
| NH$_4$Cl | ammonium chloride |
| NMR | nuclear magnetic resonance |
| Rf | retardation factor |
| THF | tetrahydrofuran |

Example 1

Intermediate

[3-(4-Hydroxy-phenyl)-isoxazol-4-yl]-carbamic acid tert-butyl ester

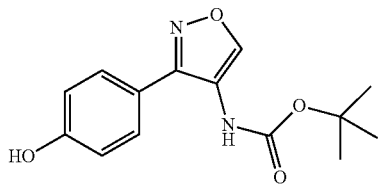 [SMILES: CC(C)(C)OC(=O)Nc1conc1-c1ccc(O)cc1]

To a solution of 4-hydroxybenzaldehyde (10 g, 81.9 mmol) in DMF (200 mL) was added K$_2$CO$_3$ (14.7 g, 106 mmol), tetrabutylammonium iodide (3.06 g, 8.2 mmol) and 4-methoxybenzyl chloride (14.1 g, 90 mmol). The reaction mixture was stirred for 14 h at rt and then poured into ice water. The product 4-(4-methoxy-benzyloxy)-benzaldehyde was isolated by filtration.

To a suspension of 4-(4-methoxy-benzyloxy)-benzaldehyde (26.5 g, 110 mmol) in water/ethanol (260 mL, 9:1) was added hydroxylamine hydrochloride (9.06 g, 131 mmol) followed by dropwise addition of a 3.2M NaOH solution in ethanol/water (88 mL; 262 mmol). After addition was complete, the reaction mixture was heated to 88° C. for 4.5 h and then cooled to rt. The pH of the reaction mixture was adjusted to 5.5 with glacial acetic acid. 4-(4-methoxy-benzyloxy)-benzaldehyde oxime (23.8 g, 84%) was isolated as a white solid by filtration and air drying.

To a solution of 4-(4-methoxy-benzyloxy)-benzaldehyde oxime (23.8 g, 92.5 mmol) in DMF (90 mL) under nitrogen was added N-chlorosuccinimide (13.6 g, 102 mmol). After starting material was consumed (as determined by TLC) the reaction mixture was transferred to a separatory funnel containing ethyl acetate and ice water. The organic phase was dried over Na$_2$SO$_4$, filtered and concentrated to give a sticky white solid.

The aforementioned solid was suspended in diethyl ether (450 mL) and to the suspension was added dropwise over 90 min a solution of triethylamine (15.47 mL, 111 mmol) and ethyl-3-(dimethylamino)acrylate (26.8 g, 185 mmol) in 50 mL of diethyl ether. After stirring overnight the reaction mixture was filtered to remove solids and the resulting solution was concentrated to yield a yellow oil. The product, 3-[4-(4-methoxy-benzyloxy)-phenyl]-isoxazole-4-carboxylic acid ethyl ester (19.77 g, 60%), was isolated by chromatography (50% ethyl acetate in hexane).

To a solution of 3-[4-(4-methoxy-benzyloxy)-phenyl]-isoxazole-4-carboxylic acid ethyl ester (19.77 g, 56 mmol) in THF (130 mL) was added 0.5M aqueous KOH solution (220 mL, 110 mmol) and the suspension was allowed to stir for 2 h. The resulting orange solution was poured into 4N aqueous HCl and 3-[4-(4-methoxy-benzyloxy)-phenyl]-isoxazole-4-carboxylic acid (16.16 g, 89%) was collected as a solid and dried azeotropically with toluene and subsequently in vacuo.

To a solution of 3-[4-(4-methoxy-benzyloxy)-phenyl]-isoxazole-4-carboxylic acid (16.16 g, 49.7 mmol) in DMF (50 mL) was added diphenylphosphoryl azide (15.04 g, 54.6 mmol) and triethylamine (7.62 mL, 54.64 mmol). The orange solution was heated to 50° C. and allowed to stir 3.5 h. At this time, tert-butanol (100 mL) was added and the reaction mixture was heated to 84° C. for 14 h after which it was cooled to rt. Concentration in vacuo gave a dark orange oil from which {3-[4-(4-methoxy-benzyloxy)-phenyl]-isoxazol-4-yl}-carbamic acid tert-butyl ester (3.01 g, 15%) was isolated by chromatography (25-50% ethyl acetate in hexane).

To a solution of {3-[4-(4-methoxy-benzyloxy)-phenyl]-isoxazol-4-yl}-carbamic acid tert-butyl ester (3.01 g, 7.6 mmol) in CH$_2$Cl$_2$ (80 mL) and water (8 mL) was added 2,3-dichloro-5,6-dicyano-1,4-benzoquinone (5.17 g, 23 mmol). After stirring for 60 h, the reaction mixture was suspended between a water/CH$_2$Cl$_2$ bilayer. The organic phase was removed and the aqueous phase was extracted twice with CH$_2$Cl$_2$. The combined organic phases were dried over Na$_2$SO$_4$, filtered and concentrated in vacuo to give a deep red oil. [3-(4-Hydroxy-phenyl)-isoxazol-4-yl]-carbamic acid tert-butyl ester (2.14 g, 92%) was isolated by chromatography (1-100% ethyl acetate in hexanes).

[3-(4-hydroxy-phenyl)-isoxazol-4-yl]-carbamic acid tert-butyl ester was dissolved in 4N HCl in dioxane and stirred for 2 hours. Removal of volatiles under reduced pressure gave a gummy solid which was suspended in 1.0 M NaHCO$_3$ solution and extracted three times with ethyl acetate. The combined organic phases were washed with brine and dried over MgSO$_4$. Filtration followed by removal of volatiles under reduced pressure gave as a white solid.

Example 2

3-[4-(4-Fluoro-benzyloxy)-phenyl]-isoxazol-4-ylamine

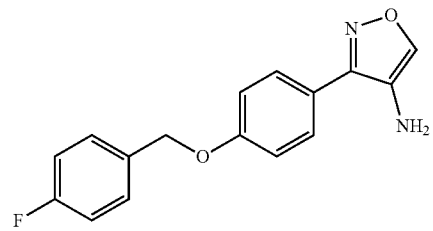 [SMILES: Nc1conc1-c1ccc(OCc2ccc(F)cc2)cc1]

To a mixture of 4-hydroxybenzaldehyde (12.2 g, 100 mmol) and K$_2$CO$_3$ (16.6 g, 120 mmol) in DMF (60 mL) was added 4-fluorobenzyl bromide (13.5 mL, 108 mmol) dropwise over 15 min. The brown suspension was warmed to 55° C. for 45 min. The reaction was then cooled to rt and poured into 500 mL ice water. 4-(4-Fluoro-benzyloxy)-benzaldehyde (21.9 g, 95%) was collected as a white solid by filtration.

To a suspension of 4-(4-fluoro-benzyloxy)-benzaldehyde (21.9 g, 95.2 mmol) and hydroxylamine hydrochloride (7.3 g, 105 mmol) in 400 mL water/ethanol 9:1 was added a solution of NaOH (9.5 g in 100 mL of water) dropwise over 15 min. The now yellow solution was stirred for 2 h at rt after which the reaction was adjusted to pH 5-6 with acetic acid. The resulting white precipitate was collected by filtration and washed with water. The wet filter cake was dissolved in ethyl acetate and dried over $Na_2SO_4$. Filtration followed by removal of volatiles under reduced pressure gave 4-(4-fluoro-benzyloxy)-benzaldehyde oxime (23.5 g, 95.8 mmol) as a yellowish crystalline solid.

To a solution of 4-(4-fluoro-benzyloxy)-benzaldehyde oxime (23.5 g, 95.8 mmol) in DMF (80 mL) was added N-chlorosuccinimide (1.27 g, 9.5 mmol) and the reaction was stirred at rt for 1 h. Then the rest of N-chlorosuccinimide (11.5 g, 86.1 mmol) was added in one portion. Following an exotherm, the reaction mixture was cooled to rt and stirred for 30 min. The reaction was poured onto 600 mL of ice water and extracted twice with ethyl acetate. The combined organic phases were washed twice with brine and dried over $Na_2SO_4$. Filtration followed by removal of volatiles under reduced pressure gave a yellow crystalline solid (27.4 g) which was dissolved in diethyl ether (250 mL) and was treated with a solution of ethyl 3-dimethylaminoacrylate (22.4 g, 156.6 mmol) and $Et_3N$ (19.2 mL, 138 mmol) in diethyl ether (250 mL) which was added dropwise over 2.5 h and then stirred overnight at rt. The suspension was filtered and concentration of the filtrate gave a residue from which 3-[4-(4-fluoro-benzyloxy)-phenyl]-isoxazole-4-carboxylic acid ethyl ester (19.6 g, 60%) was isolated as a gold oil by chromatography (15% ethyl acetate in hexane).

A solution of 3-[4-(4-fluoro-benzyloxy)-phenyl]-isoxazole-4-carboxylic acid ethyl ester (19.6 g, 57.5 mmol) in ethanol (65 mL) at 60° C. was treated with 2N aqueous NaOH (65 mL). After stirring for 14 h, the resulting yellow suspension was poured onto 500 mL of ice water and the mixture was adjusted to pH 2 with 4N HCl. The white suspension was removed by filtration and washed with water. The wet filter cake was dissolved in ethyl acetate and dried over $Na_2SO_4$. Filtration followed by removal of volatiles under reduced pressure gave crude material from which 3-[4-(4-fluoro-benzyloxy)-phenyl]-isoxazole-4-carboxylic acid (16.4 g, 91%) was isolated in pure form after washing twice with heptane, once with diethyl ether and dried in vacuo.

A solution of 3-[4-(4-fluoro-benzyloxy)-phenyl]-isoxazole-4-carboxylic acid (12.2 g, 39 mmol), triethylamine (5.4 mL, 38.8 mmol) in DMF (60 mL) was cooled to 4° C. and treated by dropwise addition over 15 min of diphenylphosphoryl azide (8.7 mL, 40.4 mmol). The ice bath was then removed and the reaction was stirred for 2 h at 38° C. The reaction was then cooled to rt, poured into 250 mL of ice water and extracted twice with ethyl acetate. The combined organic phases were washed once with 5% aqueous $NaHCO_3$, once with brine and dried over $Na_2SO_4$. Filtration followed by removal of volatiles under reduced pressure gave a reddish solid (12.8 g) which was dissolved in dichloroethane (60 mL) and tert-butanol (9.1 mL) and stirred overnight at 80° C. The reaction was cooled to rt and volatiles were removed. {3-[4-(4-Fluoro-benzyloxy)-phenyl]-isoxazol-4-yl}-carbamic acid tert-butyl ester (13.5 g, 90%) was isolated as a red-orange solid by chromatography (hexane/ethyl acetate/$CH_2Cl_2$ 75%/15%/10% to 0%/10%/90%).

{3-[4-(4-Fluoro-benzyloxy)-phenyl]-isoxazol-4-yl}-carbamic acid tert-butyl ester (1.97 g, 5.13 mmol) was dissolved in 30 mL of dioxane and 30 mL of 4 N HCl/dioxane was added. The reaction was stirred at rt for 4 h and allowed to stand overnight. The resulting crystalline mass was mixed with diethyl ether (20 mL) and stirred for 10 min. The suspension was filtered off and washed with a total of 20 mL of diethyl ether. The filter cake was partitioned between ethyl acetate and 5% $NaHCO_3$ solution and the organic phase separated. The aqueous phase was extracted with once more with ethyl acetate. The combined organic phases were washed twice with brine and dried over $Na_2SO_4$. Filtration followed by removal of volatiles under reduced pressure gave 3-[4-(4-fluoro-benzyloxy)-phenyl]-isoxazol-4-ylamine (1.32 g, 91%) as an off-white solid. M+1=285.2

Example 3

3-(4-Benzyloxy-phenyl)-isoxazol-4-ylamine

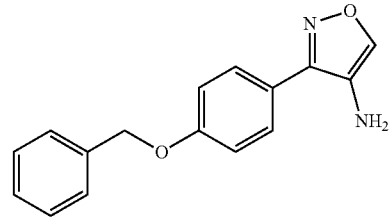 [SMILES: Nc1conc1-c1ccc(OCc2ccccc2)cc1]

4-Benzyloxybenzaldehyde was converted to 3-(4-benzyloxy-phenyl)-isoxazol-4-ylamine by methods analogous to those described in Example 2. M+1=267.2

Example 4

3-[4-(4-Methoxy-benzyloxy)-phenyl]-isoxazol-4-ylamine

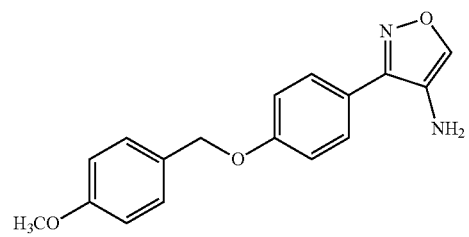 [SMILES: COc1ccc(COc2ccc(-c3nocc3N)cc2)cc1]

A solution of 3-[4-(4-methoxy-benzyloxy)-phenyl]-isoxazole-4-carboxylic acid (1.0 g, 3.07 mmol) and triethylamine (0.5 mL, 3.4 mmol) in DMF (30 mL) was cooled to 0° C. Diphenylphosphorylazide (0.8 mL, 3.86 mmol) was added and the reaction mixture was warmed to 45-60° C. for 2 h. Water (15 mL) was then added and the reaction temperature increased to 90° C. for 28 h. The reaction mixture was cooled and 3-[4-(4-methoxy-benzyloxy)-phenyl]-isoxazol-4- ylamine was isolated by chromatography (5-40% ethyl acetate in hexane) as a white solid. m.p. 92-98° C. HRMS+1=297.123

Example 5

4-[4-(4-Amino-isoxazol-3-yl)-phenoxymethyl]-benzoic acid methyl ester hydrochloride

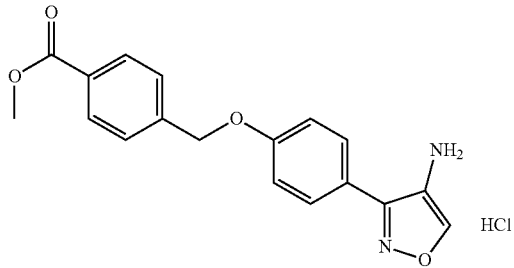 [SMILES: COC(=O)c1ccc(COc2ccc(-c3nocc3N)cc2)cc1 ; Cl]

To a suspension of [3-(4-hydroxy-phenyl)-isoxazol-4-yl]-carbamic acid tert-butyl ester, $K_2CO_3$ (1.5 equivalents), and tetrabutylammonium iodide (0.25 equivalents) in N-methylpyrrolidinone (10 volumes) was added methyl 4-(bromomethyl)benzoate (1.2 equivalents). The reaction mixture was stirred at 50'C for 16 hours (reaction progress monitored by LCMS). N-Methylpyrrolidinone was removed by evaporation, and 4-[4-(4-tert-butoxycarbonylamino-isoxazol-3-yl)-phenoxymethyl]-benzoic acid methyl ester was purified by preparative HPLC.

4-[4-(4-tert-Butoxycarbonylamino-isoxazol-3-yl)-phenoxymethyl]-benzoic acid methyl ester was suspended in 4N hydrochloric acid in dioxane (20 volumes) and stirred at rt for 16 hours (reaction progress monitored by TLC). The solvent was removed by evaporation to give 4-[4-(4-amino-isoxazol-3-yl)-phenoxymethyl]-benzoic acid methyl ester as the hydrochloride salt, which required no further purification. M+1=325.2

Example 6

3-[4-(4-Methanesulfonyl-benzyloxy)-phenyl]-isoxazol-4-ylamine

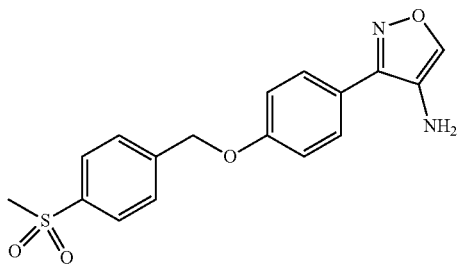 [SMILES: CS(=O)(=O)c1ccc(COc2ccc(-c3nocc3N)cc2)cc1]

To a solution of [3-(4-hydroxy-phenyl)-isoxazol-4-yl]-carbamic acid tert-butyl ester (50 mg, 0.181 mmol), $K_2CO_3$ (38 mg, 0.27 mmol) in DMF (3.0 mL) was added 4-methylsulfonylbenzyl bromide (50 mg, 0.20 mmol). The mixture was stirred for 12 h at 55° C. and then worked up and {3-[4-(4-methanesulfonyl-benzyloxy)-phenyl]-isoxazol-4-yl}-carbamic acid tert-butyl ester was purified according to methods described in Example 5.

{3-[4-(4-Methanesulfonyl-benzyloxy)-phenyl]-isoxazol-4-yl}-carbamic acid tert-butyl ester (20.5 mg, 0.046 mmol) was dissolved in a 2M HCl in dioxanes (5 mL, 10 mmol) and stirred at rt until no starting material remained. Removal of volatiles under reduced pressure and workout according to Example 2 provided 3-[4-(4-methanesulfonyl-benzyloxy)-phenyl]-isoxazol-4-ylamine (14.5 mg, 91%). HRMS (M+1)=345.09

Example 7

3-{4-[(4-methanesulfonyl-phenylamino)-methyl]-phenyl}-isoxazol-4-ylamine hydrochloride

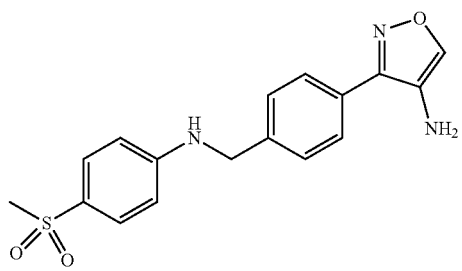 [SMILES: CS(=O)(=O)c1ccc(NCc2ccc(-c3nocc3N)cc2)cc1]

To a solution of 4-cyanobenzaldehyde (3.93 g, 30 mmol) in ethanol (100 mL) was added hydroxylamine hydrochloride (4.17 g, 60 mmol) and pyridine (4.84 mL, 60 mmol). After stirring for 2 h, all volatiles were removed under reduced pressure to give a white solid which was used without further purification.

Oxime was converted to oximinoyl chloride according to the method described in Example 1 and was isolated in crude form as a white solid and dissolved in diethyl ether (200 mL). To the solution was added dimethylaminoethyl acrylate (5.0 mL, 33 mmol) and triethylamine (4.6 mL, 33 mmol). After stirring at rt for 60 h, the reaction mixture was poured into saturated $NH_4Cl$ solution and extracted three times with diethyl ether. The combined organic phases were washed with brine and dried over $MgSO_4$. Filtration followed by removal of volatiles under reduced pressure afforded a heavy oil which was dissolved in THF (200 mL) and ethanol (100 mL) and treated with 1M aqueous NaOH (60 mL). After stirring for 4 h, the reaction mixture was poured into 1M $KHSO_4$ and extracted three times with ethyl acetate. The combined organic phases were washed with brine and dried over $MgSO_4$. Filtration followed by removal of volatiles under reduced pressure afforded 3-(4-cyano-phenyl)-isoxazole-4-carboxylic acid as a white solid (4.7 g, 73% from 4-cyanobenzaldehyde).

A solution of 3-(4-cyano-phenyl)-isoxazole-4-carboxylic acid (4.7 g, 22 mmol) in tert-butanol was treated with diphenylphosphoryl azide (5.1 mL, 24 mmol) and triethylamine (3.33 mL, 24 mmol). The solution was heated to 80° C. for 14 h and then all volatiles were removed under reduced pressure to give [3-(4-cyano-phenyl)-isoxazol-4-yl]-carbamic acid tert-butyl ester (2.1 g, 33%).

A solution of [3-(4-cyano-phenyl)-isoxazol-4-yl]-carbamic acid tert-butyl ester (1.88, 6.6 mmol) in toluene (50 mL) was cooled to 0° C. under Ar. DIBAL (6.7 mL, 1M in $CH_2Cl_2$, 6.7 mmol) was added dropwise to the solution and the reaction mixture was allowed to warm to rt and stirred for 1 h. DIBAL (6.7 mL, 1M in $CH_2Cl_2$, 6.7 mmol) was added again and the reaction mixture was stirred an additional 30 min. Saturated, aqueous Rochelle salt was added and the reaction mixture was stirred overnight. The phases were extracted three times with ethyl acetate. The combined organic phases were washed with brine and dried over $MgSO_4$. Filtration followed by removal of volatiles under reduced pressure afforded a waxy solid from which [3-(4-Formyl-phenyl)-isoxazol-4-yl]-carbamic acid tert-butyl ester was isolated as a white solid (1.34 g, 70%) by column chromatography (50% ethyl acetate in hexane).

To a solution of [3-(4-formyl-phenyl)-isoxazol-4-yl]-carbamic acid tert-butyl ester (30 mg, 0.1 mmol) and 4-methanesulfonylaniline (30 mg, 0.17 mmol) in 1,2-dichloroethane (1 mL) was added sodium trisacetoxy borohydride (50 mg, 0.23 mmol). The reaction mixture was stirred for 14 h and then loaded directly on a silica gel column. Elution with 33% hexane in ethyl acetate provided (3-{4-[(4-methanesulfonyl-phenylamino)-methyl]-phenyl}-isoxazol-4-yl)-carbamic acid tert-butyl ester as a waxy solid. This was dissolved in 4M HCl in dioxane and stirred for 1 h. Removal of volatiles under reduced pressure afforded 3-{4-[(4-methanesulfonyl-phenylamino)-methyl]-phenyl}-isoxazol-4-ylamine hydrochloride as a white solid. MH+=344.3

Example 8

3-[4-(2-Chloro-4-methanesulfonyl-benzyloxy)-phenyl]-isoxazol-4-ylamine

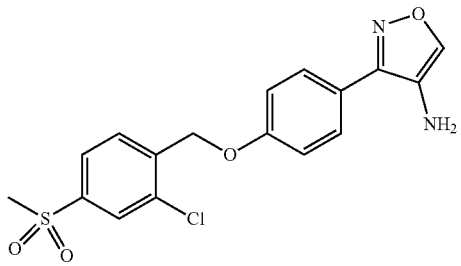 [SMILES: CS(=O)(=O)c1ccc(COc2ccc(-c3nocc3N)cc2)c(Cl)c1]

To a solution of 1-bromomethyl-2-chloro-4-methanesulfonyl-benzene (68 mg, 0.24 mmol) and 4-(4-amino-isoxazol-3-yl)-phenol (42 mg, 0.24 mmol) in $CH_3CN$ (2 mL) was added $K_2CO_3$ (66 mg, 0.48 mmol). After stirring at rt for 4 h, the reaction mixture was heated for 2 h. The reaction mixture was then cooled and all volatiles were removed under reduced pressure. From the resulting residue, 3-[4-(2-chloromethanesulfonyl-benzyloxy)-phenyl]-isoxazol-4-ylamine (40 mg, 44%) was isolated by chromatography (50-75% ethyl acetate in hexane) to yield a waxy solid. MH+=379.2

Example 9

3-{4-[2-(4-Methanesulfonyl-phenyl)-ethyl]-phenyl}-isoxazol-4-ylamine

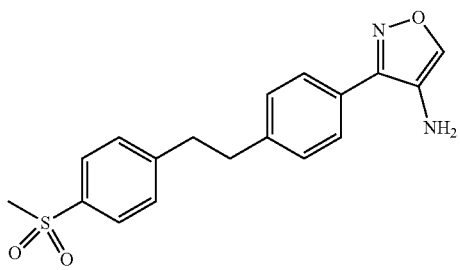 [SMILES: CS(=O)(=O)c1ccc(CCc2ccc(-c3nocc3N)cc2)cc1]

A solution of 1-chloromethyl-4-methanesulfonyl-benzene (2.0 g, 9.77 mmol) and triphenylphosphine (2.56 g, 9.77 mmol) in toluene (20 mL) was refluxed 23.5 h. The reaction mixture was filtered and the filtrate was washed with toluene and air dried to yield the phosphonium salt as a white solid.

To a solution of the aforementioned phosphonium salt in $CH_3OH$ (5 mL) was added sodium methoxide (200 mg, 3.7 mmol) to yield a yellow color. After 10 min, [3-(4-formyl-phenyl)-isoxazol-4-yl]-carbamic acid tert-butyl ester (2.56 g, 9.77 mmol) was added and the reaction mixture was heated to 65° C. for 2.5 h and rt for 15 h. Volatiles were removed under reduced pressure and the reaction was partitioned between $CH_2Cl_2$ and water. The organic phase was dried over $Na_2SO_4$, filtered and evaporated over silica gel. Chromatography afforded (3-{4-[(Z)-2-(4-Methanesulfonyl-phenyl)-vinyl]-phenyl}-isoxazol-4-yl)-carbamic acid tert-butyl ester (271 mg, 37%).

To a solution of (3-{4-[(Z)-2-(4-Methanesulfonyl-phenyl)-vinyl]-phenyl}-isoxazol-4-yl)-carbamic acid tert-butyl ester (220 mg, 0.5 mmol) in $CH_2Cl_2$ (2 mL) was added triethylamine (0.7 mL, 5 mmol) and 2-nitrobenzenesulfhydrazide (1.0 g, 4.6 mmol). The reaction mixture was stirred for 24 h at rt and then washed with satd $NaHCO_3$ and dried over $Na_2SO_4$. Filtration was followed by removal of volatiles over silica gel followed by column chromatography to yield (3-{4-[2-(4-methanesulfonyl-phenyl)-ethyl]-phenyl}-isoxazol-4-yl)-carbamic acid tert-butyl ester (88 mg, 40%) as a white solid.

(3-{4-[2-(4-Methanesulfonyl-phenyl)-ethyl]-phenyl}-isoxazol-4-yl)-carbamic acid tert-butyl ester (88 mg, 0.2 mmol) was dissolved in dioxane (2 mL) and 4N HCl in dioxane (4 mL) was added dropwise. The reaction mixture was stirred at rt for 24.5 h and 3-{4-[2-(4-methanesulfonyl-phenyl)-ethyl]-phenyl}-isoxazol-4-ylamine hydrochloride (53 mg, 71%) was collected by filtration as a white solid. HRMS: 343.111 (M+1)

Example 10

3-(5-Phenethyloxy-pyridin-2-yl)-isoxazol-4-ylamine

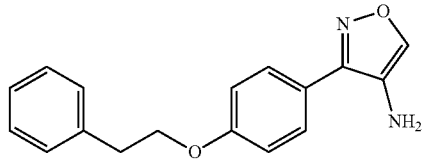 [SMILES: Nc1conc1-c1ccc(OCCc2ccccc2)cc1]

To a solution of [3-(4-hydroxy-phenyl)-isoxazol-4-yl]-carbamic acid tert-butyl ester (68 mg, 0.247 mmol), phenethyl alcohol (30 μL, 0.25 mmol)) and triphenylphosphine (136 mg, 0.52 mmol) in THF (1.5 mL) at 0° C. was added diethylazodicarboxylate (100 μL, 0.55 mmol) over 1.5 h. The reaction mixture was warmed to 90° C. for 62 h and cooled to rt. Volatiles were removed under reduced pressure and the crude product was dry-loaded onto silica gel. Chromatography provided [3-(5-phenethyloxy-pyridin-2-yl)-isoxazol-4-yl]-carbamic acid tert-butyl ester (60 mg, 64%).

[3-(5-Phenethyloxy-pyridin-2-yl)-isoxazol-4-yl]-carbamic acid tert-butyl ester (60 mg, 0.158 mmol) was dissolved in dioxane (9 mL) and treated with conc. HCl (1.8 mL). After stirring for 14 h, the reaction mixture combined with satd aqueous $NaHCO_3$ (10 mL). The organic layer was separated and dried over $Na_2SO_4$. Filtration followed by removal of volatiles under reduced pressure gave a beige solid from which 3-(5-phenethyloxy-pyridin-2-yl)-isoxazol-4-ylamine (9.8 mg, 22%) was isolated by chromatography (30% ethyl acetate in hexane). HRMS: 281.1285 (M+1).

Example 11

3-[4-(3-Phenyl-propoxy)-phenyl]-isoxazol-4-ylamine

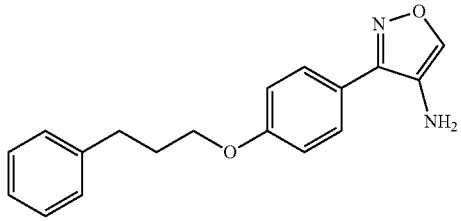 [SMILES: Nc1conc1-c1ccc(OCCCc2ccccc2)cc1]

To a solution of [3-(4-hydroxy-phenyl)-isoxazol-4-yl]-carbamic acid tert-butyl ester (38 mg, 0.137 mmol) in DMF (1 mL) was added K$_2$CO$_3$ (20 mg, 0.145 mmol) and 3-phenyl-1-bromopropane (20 μL, 0.132 mmol). After stirring for 1 h at rt and 14 h at 50° C., the reaction mixture was cooled stirred for 6 h at rt. The reaction mixture was loaded directly onto silica gel. {3-[4-(3-Phenyl-propoxy)-phenyl]-isoxazol-4-yl}-carbamic acid tert-butyl ester was isolated as a white solid by column chromatography (10% ethyl acetate in hexane).

{3-[4-(3-Phenyl-propoxy)-phenyl]-isoxazol-4-yl}-carbamic acid tert-butyl ester (54 mg, 0.137 mmol) was dissolved in dioxane (9 mL) and treated with conc. HCl (1.5 mL). After stirring for 12 h at rt the reaction mixture was quenched with 10 mL of satd aqueous NaHCO$_3$. The organic layer was separated and dried over Na$_2$SO$_4$. Filtration followed by removal of volatiles under reduce d pressure gave crude product. 3-[4-(3-Phenyl-propoxy)-phenyl]-isoxazol-4-ylamine (22 mg, 55%) was isolated as a white solid by column chromatography (30% ethyl acetate in hexanes). HRMS: 295.144 (M+1).

Example 12

3-[5-(4-Methanesulfonyl-benzyloxy)-pyridin-2-yl]-isoxazol-4-ylamine

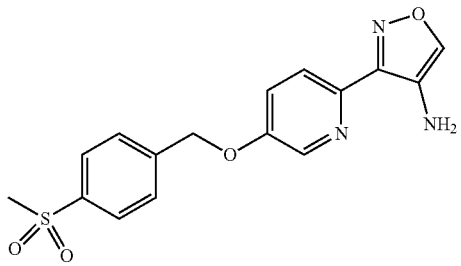 [SMILES: CS(=O)(=O)c1ccc(COc2ccc(-c3nocc3N)nc2)cc1]

To a solution of 6-methyl-pyridin-3-ol (6.0 g, 55 mmol) in DMF (100 mL) was added K$_2$CO$_3$ (7.6 g, 55 mmol), tetrabutylammonium iodide (200 mg, 0.54 mmol) and 4-(methylsulfonyl)benzyl chloride (12.4 g, 60.6 mmol) were added. The reaction mixture was stirred at rt for 20 h and then poured into 200 mL of ice water. After stirring for 15 min, 5-(4-methanesulfonyl-benzyloxy)-2-methyl-pyridine (9.76 g, 64%) was collected by vacuum filtration as a brown crystalline solid.

To a solution of 5-(4-methanesulfonyl-benzyloxy)-2-methyl-pyridine (9.76 g, 35 mmol) in chloroform (200 mL) at 0° C. was added mCPBA (7.14 g, 41.4 mmol). After 1 h, the reaction mixture was washed with 10% aqueous Na$_2$CO$_3$ and the organic layer was dried over Na$_2$SO$_4$. Filtration followed by removal of volatiles under reduced pressure gave the crude product as an orange solid.

Acetic anhydride was heated to 80° C. and the aforementioned orange solid was added. The resulting solution was heated to 130° C. for 30 min, cooled and poured into 400 mL of ice water to give a green-brown suspension which was extracted three times with ethyl acetate.

The combined organic phases were dried over Na$_2$SO$_4$, filtered and volatiles were removed under reduced pressure. Acetic acid 5-(4-methanesulfonyl-benzyloxy)-pyridin-2-ylmethyl ester (10.4 g, 88%) was isolated by chromatography (90% ethyl acetate in hexane) as a yellow solid Acetic acid 5-(4-methanesulfonyl-benzyloxy)-pyridin-2-ylmethyl ester (10.4 g, 31 mmol) was suspended in a water (20 mL) and ethanol (80 mL). To this was added NaOH (2.2 g, 55 mmol) and the reaction was heated to reflux for 2 h. The reaction mixture was cooled to rt and stirred for 24 h and then concentrated under reduced pressure. The resulting residue was partitioned between water and ethyl acetate. The organic layer was dried over Na$_2$SO$_4$, filtered and volatiles were removed under reduced pressure to yield [5-(4-methanesulfonyl-benzyloxy)-pyridin-2-yl]-methanol (4.04 g, 44%) as a light yellow solid.

Manganese dioxide (14.0 g, 161 mmol) was added to a solution of [5-(4-methanesulfonyl-benzyloxy)-pyridin-2-yl]-methanol (4.04 g, 13.77 mmol) in chloroform. The resulting mixture was heated to 60° C. for 10 min after which it was filtered through Celite and the filtrate washed with CH$_2$Cl$_2$. Volatiles were removed under reduced pressure. The crude mixture was dry-loaded onto silica gel and 5-(4-methanesulfonyl-benzyloxy)-pyridine-2-carbaldehyde (2.44 g, 61%) was isolated by chromatography (60% ethyl acetate in hexane).

To a solution of 5-(4-methanesulfonyl-benzyloxy)-pyridine-2-carbaldehyde (2.44 g, 8.4 mmol) in ethanol (1.5 mL) at 0° C. was added dropwise a solution of hydroxylamine hydrochloride (1.2 g) and NaHCO$_3$ (1.6 g) in water (15 mL) and stirred at rt for 14 h. The reaction mixture was then filtered and the filtrate air-dried to yield 5-(4-methanesulfonyl-benzyloxy)-pyridine-2-carbaldehyde oxime (2.13 g, 83%) as a white solid.

5-(4-Methanesulfonyl-benzyloxy)-pyridine-2-carbaldehyde oxime was converted to {3-[5-(4-methanesulfonyl-benzyloxy)-pyridin-2-yl]-isoxazol-4-yl}-carbamic acid tert-butyl ester by methods described in the synthesis of [3-(4-hydroxy-phenyl)-isoxazol-4-yl]-carbamic acid tert-butyl ester.

{3-[5-(4-methanesulfonyl-benzyloxy)-pyridin-2-yl]-isoxazol-4-yl}-carbamic acid tert-butyl ester (70 mg, 0.16 mmol) was dissolved in dioxane (1.5 mL) and treated with 4N HCl in dioxane (1.5 mL, 1.5 mmol). After stirring for 1.5 h, the product 3-[5-(4-methanesulfonyl-benzyloxy)-pyridin-2-yl]-isoxazol-4-ylamine hydrochloride (43 mg, 78%) was isolated as a white solid by filtration. M+1=346.0

Example 13

3-[4-(4-Methanesulfonyl-benzyloxy)-phenyl]-5-methyl-isoxazol-4-ylamine

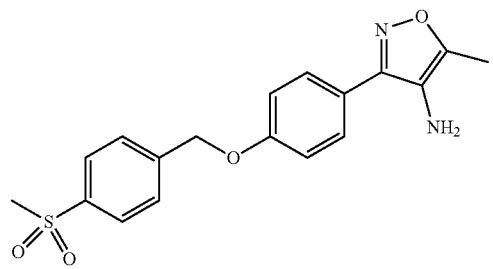

To a solution of 4-(4-methanesulfonyl-benzyloxy)-benzaldehyde oxime (4.65 g, 15.2 mmol; made using methods described in Example 2) in DMF (10 mL) was added N-chlorosuccinimide (2.60 g, 19.5 mmol) portionwise over 30 min. The mixture was then cooled to 0° C. after which it was allowed to return to rt and stirred for 1 h. The reaction mixture was poured into ice water and extracted with ethyl acetate. The organic layer was evaporated to yield a white solid which was suspended in THF (60 mL). Ethyl 3-(1-pyrrolidino)-crotonate (3.65 g, 19.9 mmol) and triethylamine (4 mL, 28.7 mmol) in THF (20 mL) were added to the suspension. After stirring for 18 h at rt the reaction mixture was concentrated in vacuo and loaded directly onto silica gel. Chromatography (35% ethyl acetate in hexane) afforded 3-[4-(4-methanesulfonyl-benzyloxy)-phenyl]-5-methyl-isoxazole-4-carboxylic acid ethyl ester (2.39 g, 38%) as a clear oil that solidified into white disks.

3-[4-(4-Methanesulfonyl-benzyloxy)-phenyl]-5-methyl-isoxazole-4-carboxylic acid ethyl ester was converted to 3-[4-(4-methanesulfonyl-benzyloxy)-phenyl]-5-methyl-isoxazol-4-ylamine by methods described in previous examples. HRMS: 359.106

Example 14

3-[4-(Pyridin-3-ylmethoxy)-phenyl]-isoxazol-4-ylamine

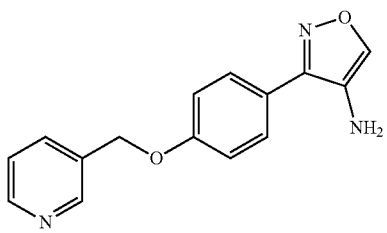 [SMILES: Nc1conc1-c1ccc(OCc2cccnc2)cc1]

To a solution of [3-(4-hydroxy-phenyl)-isoxazol-4-yl]-carbamic acid tert-butyl ester (100 mg, 0.362 mmol), 3-pyridylmethanol (40 µL, 0.42 mmol)) and triphenylphosphine (200 mg, 0.76 mmol) in THF (2.1 mL) at 0° C. was added diethylazodicarboxylate (155 µL, 0.85 mmol) over 1.5 h. The reaction mixture was warmed rt for 24 h. Volatiles were removed under reduced pressure and the crude product was dry-loaded onto silica gel. Chromatography (1-2.5% CH$_3$OH in CH$_2$Cl$_2$) provided {3-[4-(pyridin-3-ylmethoxy)-phenyl]isoxazol-4-yl}-carbamic acid tert-butyl ester.

{3-[4-(Pyridin-3-ylmethoxy)-phenyl]-isoxazol-4-yl}-carbamic acid tert-butyl ester (from previous reaction) was dissolved in dioxane (18 mL) and treated with conc. HCl (3.6 mL). After stirring for 3 h, the reaction mixture combined with satd aqueous NaHCO$_3$ (20 mL). The organic layer was separated and dried over Na$_2$SO$_4$. Filtration followed by removal of volatiles under reduced pressure gave an oily white solid from which 3-[4-(pyridin-3-ylmethoxy)-phenyl]-isoxazol-4-ylamine (6.5 mg, 6.7%) was isolated as a white solid by chromatography (5% CH$_3$OH in CH$_2$Cl$_2$). HRMS: 268.108 (M+1)

Example 15

2-[4-(4-Amino-isoxazol-3-yl)-phenoxy]-1-phenyl-ethanone hydrochloride

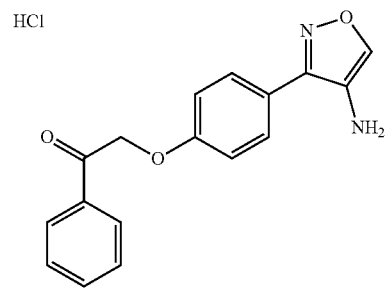 [SMILES: Cl ; Nc1conc1-c1ccc(OCC(=O)c2ccccc2)cc1]

To a solution of [3-(4-hydroxy-phenyl)-isoxazol-4-yl]-carbamic acid tert-butyl ester (50 mg, 0.18 mmol), K$_2$CO$_3$ (33 mg, 0.24 mmol) and tetrabutylammonium iodide (6.7 mg, 0.018 mmol) in DMF (2 mL) was added 2-bromoacetophenone (39.6 mg, 0.2 mmol). After 14 h the reaction mixture was poured into a water/ethyl acetate bilayer. The organic phase was concentrated and {3-[4-(2-oxo-2-phenyl-ethoxy)-phenyl]-isoxazol-4-yl}-carbamic acid tert-butyl ester (70 mg, 98%) was isolated from the resulting residue was purified by column chromatography.

{3-[4-(2-Oxo-2-phenyl-ethoxy)-phenyl]-isoxazol-4-yl}-carbamic acid tert-butyl ester (70 mg, 0.18 mmol) was dissolved in dioxane (1 mL) and treated with 4N HCl in dioxane (1 mL, 4 mmol). After stirring overnight the resulting white solid was removed by filtration and washed with hexanes to yield 2-[4-(4-Amino-isoxazol-3-yl)-phenoxy]-1-phenyl-ethanone hydrochloride as a white solid (34 mg, 64%). MH+=295.0

Example 16

3-[4-(4-Nitro-benzyloxy)-phenyl]-isoxazol-4-ylamine hydrochloride

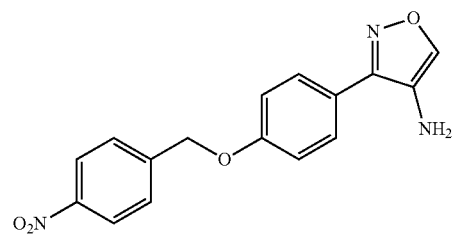 [SMILES: Nc1conc1-c1ccc(OCc2ccc([N+](=O)[O-])cc2)cc1]

Prepared by methods described in Example 5 using 4-nitrobenzyl bromide as a starting material. MH+=312.23

Example 17

4-[4-(4-Amino-isoxazol-3-yl)-phenoxymethyl]-benzonitrile hydrochloride

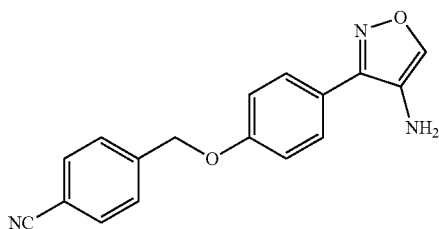 [SMILES: N#Cc1ccc(COc2ccc(-c3nocc3N)cc2)cc1]

Prepared by methods described in Example 5 using 4-cyanobenzyl bromide as a starting material. MH+=292.18

Example 18

3-[4-(4-Amino-isoxazol-3-yl)-phenoxymethyl]-benzonitrile hydrochloride

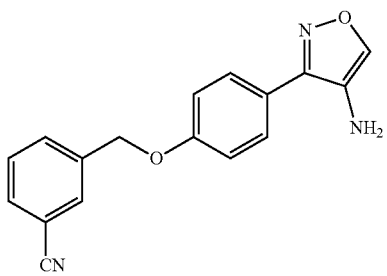 [SMILES: N#Cc1cccc(COc2ccc(-c3nocc3N)cc2)c1]

Prepared by methods described in Example 5 using 3-cyanobenzyl bromide as a starting material. MH+=292.25

Example 19

3-[4-(4-Trifluoromethyl-benzyloxy)-phenyl]-isoxazol-4-ylamine hydrochloride

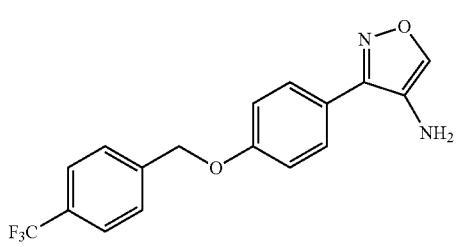 [SMILES: Nc1conc1-c1ccc(OCc2ccc(C(F)(F)F)cc2)cc1]

Prepared by methods described in Example 5 using 4-trifluoromethylbenzyl bromide as a starting material. MH+=335.2

Example 20

3-[4-(4-Trifluoromethoxy-benzyloxy)-phenyl]-isoxazol-4-ylamine hydrochloride

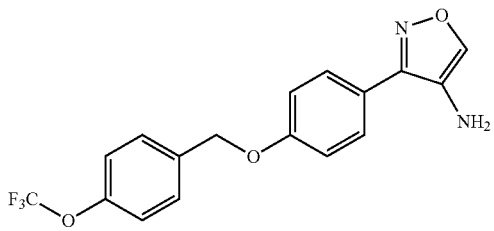 [SMILES: Nc1conc1-c1ccc(OCc2ccc(OC(F)(F)F)cc2)cc1]

Prepared by methods described in Example 5 using 4-trifluoromethoxybenzyl bromide as a starting material. MH+=351.2

Example 21

3-[4-(3,5-Difluoro-benzyloxy)-phenyl]-isoxazol-4-ylamine hydrochloride

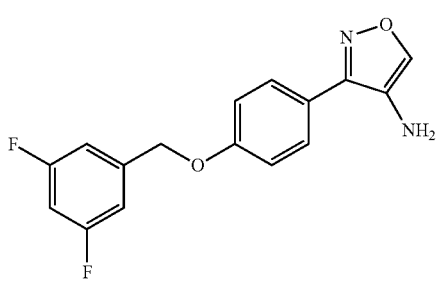 [SMILES: Nc1conc1-c1ccc(OCc2cc(F)cc(F)c2)cc1]

Prepared by methods described in Example 5 using 3,5-difluorobenzyl bromide as a starting material. MH+CH$_3$CN=344.2

Example 22

3-[4-(2-Chloro-benzyloxy)-phenyl]-isoxazol-4-ylamine hydrochloride

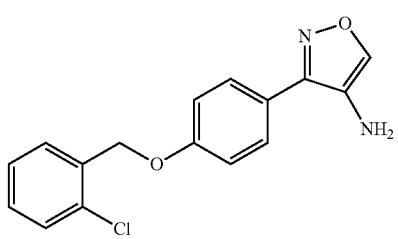 [SMILES: Nc1conc1-c1ccc(OCc2ccccc2Cl)cc1]

Prepared by methods described in Example 5 using 2-chlorobenzyl bromide as a starting material. MH+=301.1

Example 23

3-[4-(3,4-Dimethyl-benzyloxy)-phenyl]-isoxazol-4-ylamine hydrochloride

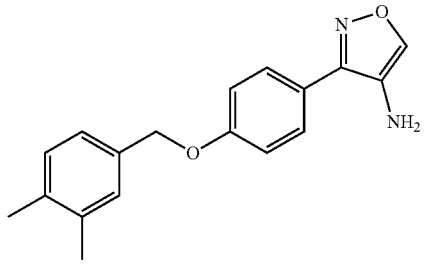 [SMILES: Cc1ccc(COc2ccc(-c3nocc3N)cc2)cc1C]

Prepared by methods described in Example 5 using 3,4-dimethylbenzyl bromide as a starting material. MH+=294.42

Example 24

3-[4-(3-Trifluoromethoxy-benzyloxy)-phenyl]-isoxazol-4-ylamine hydrochloride

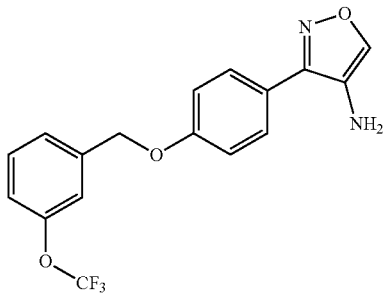 [SMILES: Nc1conc1-c1ccc(OCc2cccc(OC(F)(F)F)c2)cc1]

Prepared by methods described in Example 5 using 3-trifluoromethoxybenzyl bromide as a starting material. MH+=351.1

Example 25

3-[4-(4-Chloro-benzyloxy)-phenyl]-isoxazol-4-ylamine hydrochloride

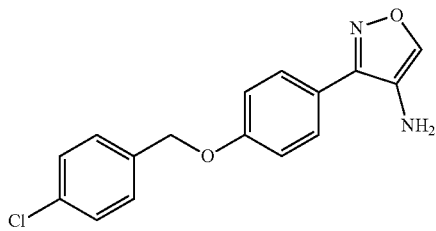 [SMILES: Nc1conc1-c1ccc(OCc2ccc(Cl)cc2)cc1]

Prepared by methods described in Example 5 using 4-chlorobenzyl bromide as a starting material. HRMS: 301.0738. m.p.=174-6° C.

Example 26

3-[4-(3,4-Dichloro-benzyloxy)-phenyl]-isoxazol-4-ylamine hydrochloride

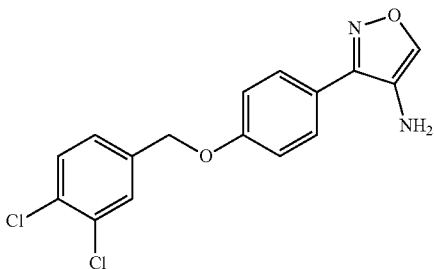 [SMILES: Nc1conc1-c1ccc(OCc2ccc(Cl)c(Cl)c2)cc1]

Prepared by methods described in Example 5 using 3,4-dichlorobenzyl bromide as a starting material. MH+=334.29

Example 27

3-[4-(4-Methyl-benzyloxy)-phenyl]-isoxazol-4-ylamine hydrochloride

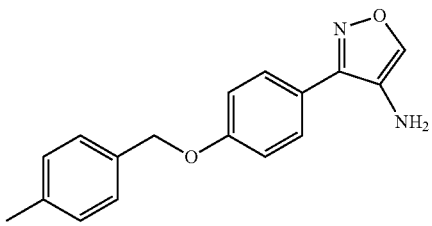 [SMILES: Cc1ccc(COc2ccc(-c3nocc3N)cc2)cc1]

Prepared by methods described in Example 6 using 4-methylbenzyl bromide as a starting material. MH+=281

Example 28

3-[4-(4-Iodo-benzyloxy)-phenyl]-isoxazol-4-ylamine

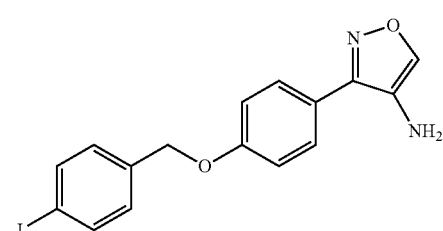

Prepared by methods described in Example 6 using 4-iodobenzyl bromide as a starting material. MH+=392.9

Example 29

3-[4-(4-Isopropyl-benzyloxy)-phenyl]-isoxazol-4-ylamine

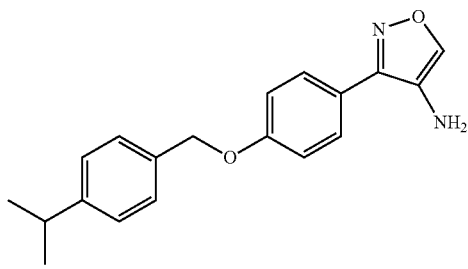 [SMILES: CC(C)c1ccc(COc2ccc(-c3nocc3N)cc2)cc1]

Prepared by methods described in Example 6 using 4-isopropylbenzyl bromide as a starting material. MH+=309

Example 30

3-[4-(4-Methanesulfonyl-benzyloxy)-phenyl]-isoxazol-4-ylamine hydrochloride

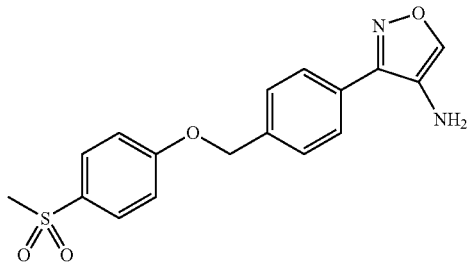 [SMILES: CS(=O)(=O)c1ccc(OCc2ccc(-c3nocc3N)cc2)cc1]

To a solution of [3-(4-hydroxymethyl-phenyl)-isoxazol-4-yl]-carbamic acid tert-butyl ester (195 mg, 0.67 mmol) in $CH_2Cl_2$ (10 mL) was added triphenylphosphine (200 mg, 0.75 mmol) and carbon tetrabromide (250 mg, 0.75 mmol). After stirring for 3 h, all volatiles were removed and the resulting residue triturated with toluene. After removing the resulting solid by filtration, all volatiles were removed and of [3-(4-bromomethyl-phenyl)-isoxazol-4-yl]-carbamic acid tert-butyl ester (74 mg, 31%) was isolated by chromatography (20% ethyl acetate in hexane).

To a solution of [3-(4-bromomethyl-phenyl)-isoxazol-4-yl]-carbamic acid tert-butyl ester (74 mg, 0.21 mmol) in DMF (1.5 mL) was added 4-methanesulfonyl phenol (41 mg, 0.24 mmol), $K_2CO_3$ (32 mg, 0.23 mmol) and tetrabutylammonium iodide (7 mg, 0.02 mmol). After stirring for 30 min, the reaction mixture was diluted with ethyl acetate and washed with water. The organic phase was dried over $Na_2SO_4$. Filtration followed by removal of volatiles under reduced pressure gave a slightly purple oil which contained residual DMF.

The aforementioned purple oil was dissolved in dioxane (1.5 mL) and treated with 4N HCl in dioxane (1.5 mL, 6 mmol). After stirring for 1 h, 3-[4-(4-methanesulfonyl-benzyloxy)-phenyl]-isoxazol-4-ylamine hydrochloride (23.4 mg, 30%) was collected by filtration as a white precipitate and dried in vacuo. M+1=345.1

Example 31

3-[4-(4-Ethanesulfonyl-benzyloxy)-phenyl]-isoxazol-4-ylamine

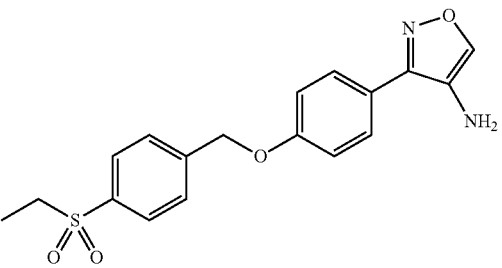 [SMILES: CCS(=O)(=O)c1ccc(COc2ccc(-c3nocc3N)cc2)cc1]

3-[4-(4-Ethanesulfonyl-benzyloxy)-phenyl]-isoxazol-4-ylamine was prepared in a manner analogous to Example 6 using 4-ethylsulfonylbenzyl bromide as a starting material. M+1=358.9

Example 32

3-[4-(1,1-Dioxo-2,3-dihydro-1H-1lambda*6*-benzo[b]thiophen-5-ylmethoxy)-phenyl]-isoxazol-4-ylamine

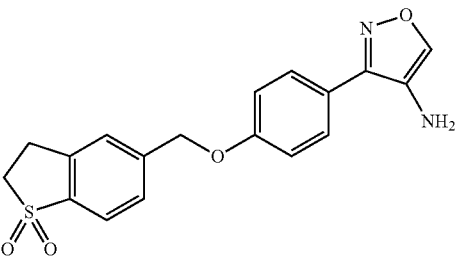 [SMILES: Nc1conc1-c1ccc(OCc2ccc3c(c2)CCS3(=O)=O)cc1]

To a solution of 5-hydroxymethyl-2,3-dihydro-benzo[b]thiophene 1,1-dioxide (185 mg, 0.93 mmol) in $CH_2Cl_2$ (6 mL) was added triphenylphosphine (294 mg, 1.12 mmol) and carbon tetrabromide (371 mg, 1.12 mmol). After stirring for 14 h at rt, all volatiles were removed under reduced pressure. 5-Bromomethyl-2,3-dihydro-benzo[b]thiophene 1,1-dioxide (218 mg, 90%) was isolated by chromatography (33-50% ethyl acetate in hexanes).

To a solution of 5-bromomethyl-2,3-dihydro-benzo[b]thiophene 1,1-dioxide (55 mg, 0.21 mmol), 4-(4-amino-isoxazol-3-yl)-phenol (37 mg, 0.21 mmol) in DMF (2 mL) was added tetrabutylammonium iodide (8 mg, 0.021 mmol) and $K_2CO_3$ (58 mg, 0.42 mmol). After stirring for 4 h at rt, the reaction mixture was poured into water and extracted three times with ethyl acetate. The combined organic layers were washed three times with water, once with brine and dried over $Na_2SO_4$. Filtration followed by removal of volatiles under reduced pressure gave crude product from which 3-[4-(1,1-dioxo-2,3-dihydro-1H-1lambda*6*-benzo[b]thiophen-5-ylmethoxy)-phenyl]-isoxazol-4-ylamine (42 mg, 56%) was isolated by chromatography (66-80% ethyl acetate in hexane. M+1=356.9

Example 33

3-[4-(1,1-Dioxo-1H-1lambda*6*-benzo[b]thiophen-5-ylmethoxy)-phenyl]-isoxazol-4-ylamine

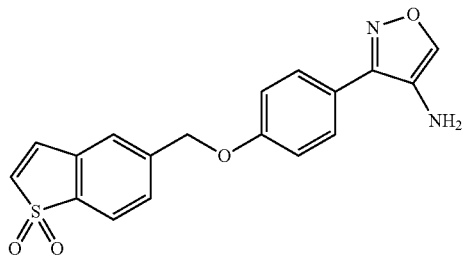 [SMILES: Nc1conc1-c1ccc(OCc2ccc3c(c2)C=CS3(=O)=O)cc1]

Prepared from (1,1-dioxo-1H-1lambda*6*-benzo[b]thiophen-5-yl)-methanol in a manner analogous to Example 32 using 5-hydroxymethyl-benzo[b]thiophene 1,1-dioxide as a starting material. M+1=355.0

Example 34

3-[4-(4-Benzenesulfonyl-benzyloxy)-phenyl]-isoxazol-4-ylamine

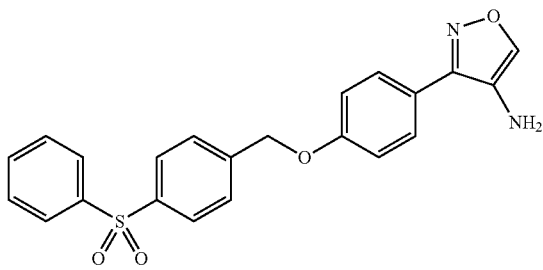 [SMILES: Nc1conc1-c1ccc(OCc2ccc(S(=O)(=O)c3ccccc3)cc2)cc1]

Prepared from (4-benzenesulfonyl-phenyl)-methanol in a manner analogous Example 32 using (4-benzenesulfonyl-phenyl)-methanol as a starting material. M+1=406.9

Example 35

3-[4-(4-Methylsulfanyl-benzyloxy)-phenyl]-isoxazol-4-ylamine hydrochloride

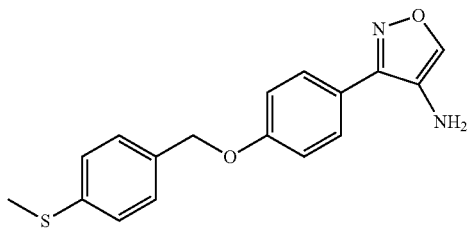 [SMILES: CSc1ccc(COc2ccc(-c3nocc3N)cc2)cc1]

Prepared by methods described in Example 5 using 4-thiomethylbenzyl bromide as a starting material. MH+=313.0

Example 36

3-[4-(4-Trifluoromethylsulfanyl-benzyloxy)-phenyl]-isoxazol-4-ylamine hydrochloride

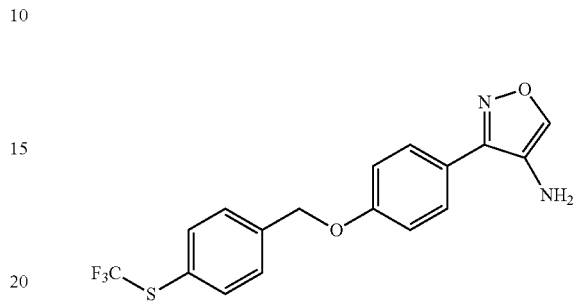

Prepared by methods described in Example 5 using 4-thiotrifluoromethylbenzyl bromide as a starting material. MH+=367.0

Example 37

Biological Assay of Representative Compounds of the Invention

Stearoyl CoA desaturase activity was monitored by a modification of the acyl carrier protein assay described by B. R. Talamo and K. Bloch in *Anal. Biochem.* 1968, 29, 300-304. The SCD assay monitors the release of tritiated water from the desaturation of 9,10-$^3$H-stearoyl CoA.

Mouse liver microsomes, prepared from mice fed a high-carbohydrate diet, were a source of the SCD and cyt b5 and cyt b5 reductase, necessary accessory proteins for the coupled reaction. Reaction mixtures for compound titrations contained 50 mM Tris HCl pH 7.5, 100 mM NaCl, 0.165 mg/mL BSA, 2.4% DMSO, 1 mM NADH, 0.03% T-20, and 300 nM (9,10) $^3$H-stearoyl CoA (Perkin-Elmer). Reactions were initiated upon the addition of 4 ug/mL SCD microsomes. Incubations were terminated after 25 minutes at rt with cold 6% TCA. After standing 10 minutes at 4° C., samples were centrifuged 15 minutes at 4000 rpm to pellet precipitated protein. Supernatants were added to microtiter plates containing suspensions of activated charcoal (Darco G-60, Fisher Scientific) and mixed by inversion. Plates were then centrifuged to separate $^3$H—H$_2$O product from charcoal-bound reactants. Supernatants were quantitated in a Perkin Elmer Topcount 384 after solubilization in ScintiSafe Plus 50% (Fisher Scientific).

Inhibition (%) of SCD activity by compounds was calculated according to the following formula:

$$\% \text{ Inhibition} = 100 * [1 - (CPM_{sample} - CPM_{blank})/(CPM_{total} - CPM_{blank})].$$

The results of the in vitro inhibition of SCD1 by certain compounds of the invention are shown in the following Table:

| Example | Name | IC$_{50}$ (nM) |
|---|---|---|
| 2 | 3-[4-(4-Fluoro-benzyloxy)-phenyl]-isoxazol-4-ylamine | 612 |
| 3 | 3-(4-Benzyloxy-phenyl)-isoxazol-4-ylamine | 464 |
| 4 | 3-[4-(4-Methoxy-benzyloxy)-phenyl]-isoxazol-4-ylamine | 104 |
| 5 | 4-[4-(4-Amino-isoxazol-3-yl)-phenoxymethyl]-benzoic acid methyl ester hydrochloride | 152 |
| 6 | 3-[4-(4-Methanesulfonyl-benzyloxy)-phenyl]-isoxazol-4-ylamine | 40 |
| 7 | 3-{4-[(4-methanesulfonyl-phenylamino)-methyl]-phenyl}-isoxazol-4-ylamine hydrochloride | 817 |
| 8 | 3-[4-(2-Chloro-4-methanesulfonyl-benzyloxy)-phenyl]-isoxazol-4-ylamine | 191 |
| 9 | 3-{4-[2-(4-Methanesulfonyl-phenyl)-ethyl]-phenyl}-isoxazol-4-ylamine | 280 |
| 10 | 3-(5-Phenethyloxy-pyridin-2-yl)-isoxazol-4-ylamine | 1930 |
| 11 | 3-[4-(3-Phenyl-propoxy)-phenyl]-isoxazol-4-ylamine | 372 |
| 12 | 3-[5-(4-Methanesulfonyl-benzyloxy)-pyridin-2-yl]-isoxazol-4-ylamine | 466 |
| 13 | 3-[4-(4-Methanesulfonyl-benzyloxy)-phenyl]-5-methyl-isoxazol-4-ylamine | 864 |
| 14 | 3-[4-(Pyridin-3-ylmethoxy)-phenyl]-isoxazol-4-ylamine | 2200 |
| 15 | 2-[4-(4-Amino-isoxazol-3-yl)-phenoxy]-1-phenyl-ethanone hydrochloride | 395 |
| 16 | 3-[4-(4-Nitro-benzyloxy)-phenyl]-isoxazol-4-ylamine hydrochloride | 264 |
| 17 | 4-[4-(4-Amino-isoxazol-3-yl)-phenoxymethyl]-benzonitrile hydrochloride | 603 |
| 18 | 3-[4-(4-Amino-isoxazol-3-yl)-phenoxymethyl]-benzonitrile hydrochloride | 315 |
| 19 | 3-[4-(4-Trifluoromethyl-benzyloxy)-phenyl]-isoxazol-4-ylamine hydrochloride | 391 |
| 20 | 3-[4-(4-Trifluoromethoxy-benzyloxy)-phenyl]-isoxazol-4-ylamine hydrochloride | 135 |
| 21 | 3-[4-(3,5-Difluoro-benzyloxy)-phenyl]-isoxazol-4-ylamine hydrochloride | 257 |
| 22 | 3-[4-(2-Chloro-benzyloxy)-phenyl]-isoxazol-4-ylamine hydrochloride | 1744 |
| 23 | 3-[4-(3,4-Dimethyl-benzyloxy)-phenyl]-isoxazol-4-ylamine hydrochloride | 148 |
| 24 | 3-[4-(3-Trifluoromethoxy-benzyloxy)-phenyl]-isoxazol-4-ylamine hydrochloride | 1350 |
| 25 | 3-[4-(4-Chloro-benzyloxy)-phenyl]-isoxazol-4-ylamine | 246 |
| 26 | 3-[4-(3,4-Dichloro-benzyloxy)-phenyl]-isoxazol-4-ylamine hydrochloride | 162 |
| 27 | 3-[4-(4-Methyl-benzyloxy)-phenyl]-isoxazol-4-ylamine hydrochloride | 196 |
| 28 | 3-[4-(4-Iodo-benzyloxy)-phenyl]-isoxazol-4-ylamine | 126 |
| 29 | 3-[4-(4-Isopropyl-benzyloxy)-phenyl]-isoxazol-4-ylamine | 161 |
| 30 | 3-[4-(4-Methanesulfonyl-benzyloxy)-phenyl]-isoxazol-4-ylamine hydrochloride | 527 |
| 31 | 3-[4-(4-Ethanesulfonyl-benzyloxy)-phenyl]-isoxazol-4-ylamine | 65 |
| 32 | 3-[4-(1,1-Dioxo-2,3-dihydro-1H-1lambda*6*-benzo[b]thiophen-5-ylmethoxy)-phenyl]-isoxazol-4-ylamine | 259 |
| 33 | 3-[4-(1,1-Dioxo-1H-1lambda*6*-benzo[b]thiophen-5-ylmethoxy)-phenyl]-isoxazol-4-ylamine | 411 |
| 34 | 3-[4-(4-Benzenesulfonyl-benzyloxy)-phenyl]-isoxazol-4-ylamine | 673 |
| 35 | 3-[4-(4-Methylsulfanyl-benzyloxy)-phenyl]-isoxazol-4-ylamine | 99 |
| 36 | 3-[4-(4-Trifluoromethylsulfanyl-benzyloxy)-phenyl]-isoxazol-4-ylamine | 51 |

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is then mixed with sodium starch glycolate and magnesium stearate and compressed to yield kernels of 120 or 350 mg respectively. The kernels are lacquered with an aq. solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

The invention claimed is:

1. A compound of formula (I)

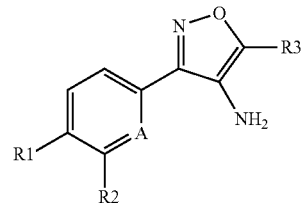

wherein

A is —CH— or nitrogen;

R1 is —O(CH$_2$)$_n$R4, —CH$_2$NHR4, —CH$_2$CH$_2$R4, —OCH$_2$C(O)R4 or —CH$_2$OR4;

R2 is hydrogen or halogen;

R3 is hydrogen or lower alkyl;

R4 is phenyl, pyridinyl, 1,1-dioxo-2,3-dihydro-1H-1lambda*6*-benzo[b]thiophenyl or 1,1-dioxo-1H-1lambda*6*-benzo[b]thiophenyl, said phenyl optionally mono- or bi-substituted independently with halogen, lower alkyl, alkoxy, —C(O)OCH$_3$, —S(O)$_2$CH$_3$, —NO$_2$, —CN, —CF$_3$, —OCF$_3$, —SCH$_3$, —SO$_2$-phenyl, —SCF$_3$ or —SO$_2$CH$_2$CH$_3$; and n is 1, 2 or 3;

or a pharmaceutically acceptable salt thereof.

2. The compound according to claim 1, wherein A is —CH—.

3. The compound according to claim 1, wherein R1 is —O(CH$_2$)$_n$R4 or —CH$_2$NHR4.

4. The compound according to claim 1, wherein R1 is —O(CH$_2$)$_n$R4.

5. The compound according to claim 1, wherein R1 is —OCH$_2$R4.

6. The compound according to claim 1, wherein R2 is hydrogen.

7. The compound according to claim 1, wherein R3 is hydrogen or methyl.

8. The compound according to claim 1, wherein R4 is unsubstituted phenyl, pyridinyl, 1,1-dioxo-2,3-dihydro-1H-1lambda*6*-benzo[b]thiophenyl or 1,1-dioxo-1H-1lambda*6*-benzo[b]thiophenyl.

9. The compound according to claim 1, wherein R4 is unsubstituted phenyl.

10. The compound according to claim 1, wherein R4 is phenyl mono-substituted with Cl, F, I, methyl, isopropyl, —OCH$_3$, —C(O)OCH$_3$, —S(O)$_2$CH$_3$, —NO$_2$, —CN, —CF$_3$, —OCF$_3$, —SCH$_3$, —SO$_2$-phenyl, —SCF$_3$ or —SO$_2$CH$_2$CH$_3$.

11. The compound according to claim 1, wherein R4 is phenyl bi-substituted independently with methyl or halogen.

12. The compound according to claim 1, selected from the group consisting of:

3-[4-(4-Fluoro-benzyloxy)-phenyl]-isoxazol-4-ylamine;

3-(4-Benzyloxy-phenyl)-isoxazol-4-ylamine;

3-[4-(4-Methoxy-benzyloxy)-phenyl]-isoxazol-4-ylamine;

4-[4-(4-Amino-isoxazol-3-yl)-phenoxymethyl]-benzoic acid methyl ester hydrochloride;

3-[4-(4-Methanesulfonyl-benzyloxy)-phenyl]-isoxazol-4-ylamine;

3-{4-[(4-methanesulfonyl-phenylamino)-methyl]-phenyl}-isoxazol-4-ylamine hydrochloride;

3-[4-(2-Chloro-4-methanesulfonyl-benzyloxy)-phenyl]-isoxazol-4-ylamine;
3-{4-[2-(4-Methanesulfonyl-phenyl)-ethyl]-phenyl}-isoxazol-4-ylamine;
3-(5-Phenethyloxy-pyridin-2-yl)-isoxazol-4-ylamine;
3-[4-(3-Phenyl-propoxy)-phenyl]-isoxazol-4-ylamine;
3-[5-(4-Methanesulfonyl-benzyloxy)-pyridin-2-yl]-isoxazol-4-ylamine;
3-[4-(4-Methanesulfonyl-benzyloxy)-phenyl]-5-methyl-isoxazol-4-ylamine;
3-[4-(Pyridin-3-ylmethoxy)-phenyl]-isoxazol-4-ylamine;
2-[4-(4-Amino-isoxazol-3-yl)-phenoxy]-1-phenyl-ethanone hydrochloride;
3-[4-(4-Nitro-benzyloxy)-phenyl]-isoxazol-4-ylamine hydrochloride;
4-[4-(4-Amino-isoxazol-3-yl)-phenoxymethyl]-benzonitrile hydrochloride;
3-[4-(4-Amino-isoxazol-3-yl)-phenoxymethyl]-benzonitrile hydrochloride;
3-[4-(4-Trifluoromethyl-benzyloxy)-phenyl]-isoxazol-4-ylamine hydrochloride;
3-[4-(4-Trifluoromethoxy-benzyloxy)-phenyl]-isoxazol-4-ylamine hydrochloride;
3-[4-(3,5-Difluoro-benzyloxy)-phenyl]-isoxazol-4-ylamine hydrochloride;
3-[4-(2-Chloro-benzyloxy)-phenyl]-isoxazol-4-ylamine hydrochloride;
3-[4-(3,4-Dimethyl-benzyloxy)-phenyl]-isoxazol-4-ylamine hydrochloride;
3-[4-(3-Trifluoromethoxy-benzyloxy)-phenyl]-isoxazol-4-ylamine hydrochloride;
3-[4-(4-Chloro-benzyloxy)-phenyl]-isoxazol-4-ylamine;
3-[4-(3,4-Dichloro-benzyloxy)-phenyl]-isoxazol-4-ylamine hydrochloride;
3-[4-(4-Methyl-benzyloxy)-phenyl]-isoxazol-4-ylamine hydrochloride;
3-[4-(4-Iodo-benzyloxy)-phenyl]-isoxazol-4-ylamine;
3-[4-(4-Isopropyl-benzyloxy)-phenyl]-isoxazol-4-ylamine;
3-[4-(4-Methanesulfonyl-benzyloxy)-phenyl]-isoxazol-4-ylamine hydrochloride;
3-[4-(4-Ethanesulfonyl-benzyloxy)-phenyl]-isoxazol-4-ylamine;
3-[4-(1,1-Dioxo-2,3-dihydro-1H-1lambda*6*-benzo[b]thiophen-5-ylmethoxy)-phenyl]-isoxazol-4-ylamine;
3-[4-(1,1-Dioxo-1H-1lambda*6*-benzo[b]thiophen-5-ylmethoxy)-phenyl]-isoxazol-4-ylamine;
3-[4-(4-Benzenesulfonyl-benzyloxy)-phenyl]-isoxazol-4-ylamine;
3-[4-(4-Methylsulfanyl-benzyloxy)-phenyl]-isoxazol-4-ylamine; and
3-[4-(4-Trifluoromethylsulfanyl-benzyloxy)-phenyl]-isoxazol-4-ylamine.

13. A pharmaceutical composition, comprising a therapeutically effective amount of a compound according to claim 1 and a pharmaceutically acceptable carrier.

14. A method for treating cancer, comprising the step of administering a therapeutically effective amount of a compound according to claim 1 to a subject in need thereof.

* * * * *